United States Patent [19]

Meilland, deceased

[11] Patent Number: Plant 6,891

[45] Date of Patent: Jul. 4, 1989

[54] ROSE PLANT—MEIFLOPAN VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 187,444

[22] Filed: Apr. 28, 1988

[51] Int. Cl.[4] ..... A01H 5/00

[52] U.S. Cl. ..... Plt./1

[58] Field of Search ..... Plt. 1

*Primary Examiner*—James R. Feyrer

*Attorney, Agent, or Firm*—Burns, Doane, Swecker & Mathis

[57] ABSTRACT

A new and distinct variety of shrub rose plant is provided which forms in the spring multiple attractive very double white blossoms per stem. The variety exhibits a semi-prostrate growth habit, and excellent resistance to diseases. An excellent aptitude for rooting and growing on its own roots is exhibited. The new variety is well adapted for growing as a landscape planting.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was *Rosa sempervirens.* The male parent (i.e., the pollen parent) of the new variety was the Marthe Carron variety (non-patented). The parentage of the new variety can be summarized as follows:

*Rosa sempervirens*×*Marthe Carron.*

The seeds resulting from the above pollination were sown and 3 plantlets were obtained which were physically and biologically different from each other. Selective study resulted in the identification of a single plant of the new variety.

It was found that the new variety of shrub rose plant of the present invention possesses the following combination of characteristics:

(a) forms in the spring attractive very double white blossoms which are borne on a multiple basis per stem,
(b) exhibits a semi-prostrate growth habit,
(c) exhibits excellent resistance to diseases,
(d) exhibits an excellent aptitude for rooting and growing on its own roots, and
(e) is particularly well suited for growing in the landscape.

The new variety well meets the needs of the horitcultural industry. It can be grown to advantage as an attractive ornamentation in parks, gardens, public areas, and residential landscapes. It is particularly well suited for growing in the landscape.

The characteristics of the new variety have been found to be homogeneous and stable and are strictly transmissible by asexual propagation such as budding, grafting, and cuttage from one generation to another.

The new variety has been named the Meiflopan variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the new variety described herein were grown in the open air during June on their own roots at Cannet-des-Maures, Var, France.

DETAILED DESCRIPTION

Figures 1, 2, 3, 4, 5, 6, 7, 8, 9, 10, 11, 12, 13, 14, 15, 16, 17, 18:
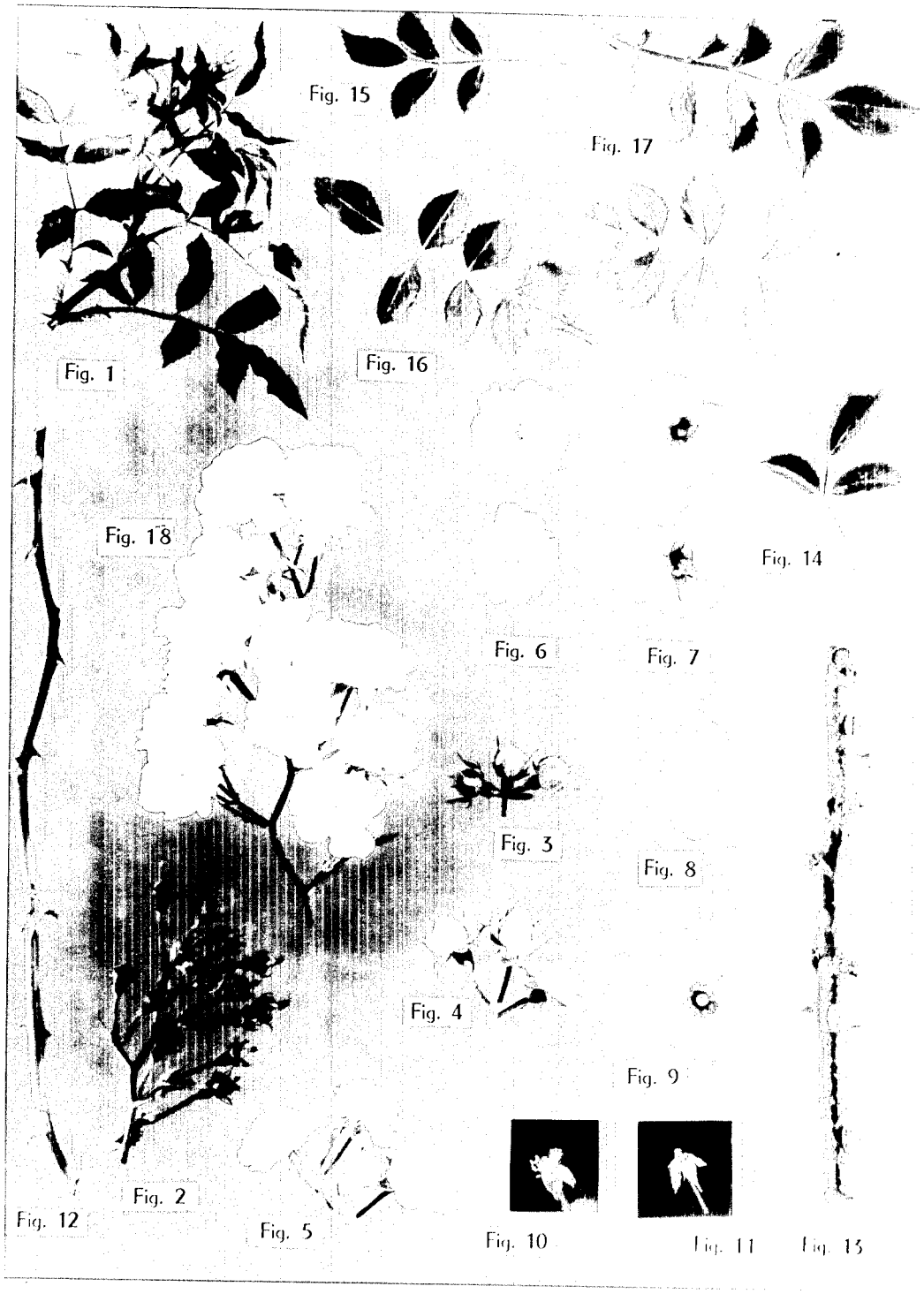
FIG. 1 illustrates a specimen of a young shoot.
FIG. 2 illustrates a specimen of floral buds before the opening of the sepals.
FIG. 3 illustrates specimens of three floral buds at the opening of the sepals.
FIG. 4 illustrates specimens of three floral buds as the petals open.
FIG. 5 illustrates specimens of three flowers in the course of opening.
FIG. 6 illustrates specimens of two fully open flowers—plan view—obverse.
FIG. 7 illustrates specimens of two fully open flowers—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—obverse.
FIG. 15 illustrates a specimen of a leaf with five leaflets—plan view—obverse.
FIG. 16 illustrates a specimen of a leaf with seven leaflets—plan view—reverse.
FIG. 17 illustrates a specimen of a leaf with nine leaflets—plan view—observe (top) and reserve (bottom)
FIG. 18 illustrates a specimen of a floral stem showing the multiple inflorescence.

The chart used in the identification of colors is that of the Royal Horticultural Society (R.H.S. Colour Chart). The description is based on three-year old specimens of the new variety during June while grown in the open air on their own roots at Cannet-des-Maures, Var, France.

Class: Shrub.

Plant:

*Height.*—Approximately 120 to 150 cm. on average.

*Habit.*—Semi-prostrate.

Branches:

*Color.*—Young stems: lettuce green, Yellow-Green Group 144A. Adult wood: light green, Yellow-Green Group 146B.

Leaves:

*Stipules.*—Adnate, pectinate, wide and notched.

*Petioles.*—Upper surface: grooved, reddish-brown on young foliage, medium green on mature foliage with very glandular edges. Under surface: medium green with many glandular aciculas.

*Leaflets.*—Number: 3, 5, 7 (most often), and 9. Shape: Elliptical. Serration: simple and regular. Texture: firm. Overall appearance: dense foliage with a glossy aspect. Color (young foliage): upper surface: lettuce green, Yellow-Green Group 144A, edged with a reddish tint. Under surface: lettuce green, Yellow-Green Group 144B, edged and more or less suffused with a reddish tint. Color (adult foliage): upper surface: dark green, Yellow-Green Group 147A. under surface: medium green, Yellow-Green Group 147B.

Inflorescence:

*Number of flowers.*—Approximately 8 to 15 blossoms per floral stem.

*Peduncle.*—Medium green, more or less shaded with red, straight, short, rigid, approximately 2 cm. in length.

*Sepals.*—Upper surface: tomentose and greenish. Under surface: medium green with small glandular edges, the outside sepals commonly have appendiculated edges.

*Buds.*—Shape: globular. Length: approximately 0.7 to 1.0 cm. on average. Size: small. Color (when opening): upper surface: white, White Group 155B. under surface: white, White Group 155B.

*Flower.*—Form: very double, initially as a hollow cup and subsequently becomes more flattened. Diameter: approximately 3.5 to 4 cm. on average. Color (when opening begins): upper surface: white, White Group 155B. under surface: white, White Group 155B. Color (when blooming): upper surface: white, White Group 155B. under surface: white, White Group 155B. Color (at end of blooming): upper surface: white, White Group 155B. under surface: white, White Group 155B. Fragrance: none. Flower duration: long. Petal form: generally oval with more or less notched margins, central petals tend to be narrow and lance-shaped. Petal texture: firm. Petal number: approximately 50 to 55 on average. Petal drop: good. Stamen number: approximately 14 to 20 on average. Anthers: normal, yellowish. Filaments: straw colored, and of irregular heights. Pistils: approximately 10 on average. Stigmas: normal, straw colored, located under the anthers. Styles: greenish, of irregular heights. Receptacle: medium green, more or less reddish in coloration at the dehiscence of the anthers, and in longitudinal section it is pear shaped.

Development:

*Vegetation.*—Vigorous.

*Blossoming.*—Abundant and continuous.

*Aptitude to bear fruits.*—Slight to none.

*Resistance to frost.*—Normal.

*Resistance to diseases.*—Very good.

It is claimed:

1. A new and distinct variety of shrub rose plant characterized by the following combination of characteristics:

(a) forms in the spring attractive very double white blossoms which are borne on a multiple basis per stem, (b) exhibits a semi-prostrate growth habit, (c) exhibits excellent resistance to diseases, (d) exhibits an excellent aptitude for rooting and growing on its own roots, and (e) is particularly well suited for growing in the landscape;

substantially as herein shown and described together with the parts thereof.

* * * * *